United States Patent
Ostrovsky et al.

(10) Patent No.: US 10,123,682 B2
(45) Date of Patent: *Nov. 13, 2018

(54) ARTICULATING TORQUEABLE HOLLOW DEVICE

(71) Applicant: Boston Scientific Scimed, Inc., Maple Grove, MN (US)

(72) Inventors: Isaac Ostrovsky, Wellesley, MA (US); Jozef Slanda, Milford, MA (US); Jeffrey Bean, Fitchburg, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/585,303

(22) Filed: May 3, 2017

(65) Prior Publication Data

US 2017/0231473 A1   Aug. 17, 2017

Related U.S. Application Data

(63) Continuation of application No. 14/834,717, filed on Aug. 25, 2015, now Pat. No. 9,668,641, which is a
(Continued)

(51) Int. Cl.
*A61B 1/00* (2006.01)
*A61B 1/005* (2006.01)
(Continued)

(52) U.S. Cl.
CPC ............ *A61B 1/0055* (2013.01); *A61B 1/008* (2013.01); *A61B 1/0057* (2013.01); *A61M 25/0141* (2013.01); *A61M 25/0147* (2013.01)

(58) Field of Classification Search
USPC .................................................. 600/139–145
See application file for complete search history.

(56) References Cited

U.S. PATENT DOCUMENTS

| | | |
|---|---|---|
| 4,852,565 A | 8/1989 | Eisele |
| 5,005,558 A | 4/1991 | Aomori |

(Continued)

FOREIGN PATENT DOCUMENTS

| | | |
|---|---|---|
| EP | 0 513 836 A1 | 11/1992 |
| JP | 4-343316 | 11/1992 |

(Continued)

OTHER PUBLICATIONS

Extended Search Report for corresponding EP Application No. 17156564.1 dated May 30, 2017 (7 pages).
(Continued)

*Primary Examiner* — Matthew J Kasztejna
(74) *Attorney, Agent, or Firm* — Bookoff McAndrews, PLLC

(57) ABSTRACT

An articulating mechanism for use in a medical device, such as an endoscope or a catheter, includes a series of stacked links disposed adjacent to one another and movable with respect to each other. Each link includes a front face tapered to a pair of pivot points and a rear face defining a wedge shaped recess for receiving the pivot points of the adjacent link. Pull-wires provide tension and hold the staked links together while also allowing for controlled bending of the distal portion by movement of one or more of the pull-wires.

17 Claims, 10 Drawing Sheets

Related U.S. Application Data continuation of application No. 13/901,936, filed on May 24, 2013, now Pat. No. 9,144,369, which is a continuation of application No. 12/121,345, filed on May 15, 2008, now Pat. No. 8,465,420.

(60) Provisional application No. 60/930,748, filed on May 18, 2007.

(51) Int. Cl.
*A61B 1/008* (2006.01)
*A61M 25/01* (2006.01)

(56) References Cited

U.S. PATENT DOCUMENTS

| | | | |
|---|---|---|---|
| 5,271,382 A | 12/1993 | Chikama |
| 5,477,856 A | 12/1995 | Lundquist |
| 5,702,754 A | 12/1997 | Zhong |
| 5,733,243 A | 3/1998 | Yabe et al. |
| 5,857,964 A | 1/1999 | Konstorum et al. |
| 5,873,817 A | 2/1999 | Kokish et al. |
| 5,916,146 A | 6/1999 | Allotta et al. |
| 5,916,147 A | 6/1999 | Boury |
| 5,938,588 A | 8/1999 | Grabover et al. |
| 6,048,620 A | 4/2000 | Zhong |
| 6,171,235 B1 | 1/2001 | Konstorum et al. |
| 6,475,140 B1 | 11/2002 | Konstorum et al. |
| 6,485,411 B1 | 11/2002 | Konstorum et al. |
| 6,599,237 B1 | 7/2003 | Singh |
| 6,656,195 B2 | 12/2003 | Peters et al. |
| 6,740,030 B2 | 5/2004 | Martone et al. |
| 6,749,560 B1 | 6/2004 | Konstorum et al. |
| 6,780,151 B2 | 8/2004 | Grabover et al. |
| 6,790,173 B2 | 9/2004 | Saadat et al. |
| 6,817,974 B2 | 11/2004 | Cooper et al. |
| 6,858,005 B2 | 2/2005 | Ohline et al. |
| 6,890,329 B2 | 5/2005 | Carroll et al. |
| 7,090,637 B2 | 8/2006 | Danitz et al. |
| 7,637,905 B2 | 12/2009 | Saadat et al. |
| 2004/0186350 A1 | 9/2004 | Brenneman et al. |
| 2004/0199052 A1 | 10/2004 | Banik et al. |
| 2004/0225186 A1 | 11/2004 | Horne, Jr. et al. |
| 2004/0236316 A1 | 11/2004 | Danitz et al. |
| 2004/0249367 A1 | 12/2004 | Saadat et al. |
| 2005/0015072 A1 | 1/2005 | Engel et al. |
| 2005/0075538 A1 | 4/2005 | Banik et al. |
| 2005/0090809 A1 | 4/2005 | Cooper et al. |
| 2005/0096694 A1 | 5/2005 | Lee |
| 2005/0107667 A1 | 5/2005 | Danitz et al. |
| 2005/0119527 A1 | 6/2005 | Banik et al. |
| 2005/0119644 A1 | 6/2005 | Koerner |
| 2005/0131279 A1 | 6/2005 | Boulais et al. |
| 2005/0182475 A1 | 8/2005 | Jen et al. |
| 2005/0272975 A1 | 12/2005 | McWeeney et al. |
| 2005/0273084 A1 | 12/2005 | Hinman et al. |
| 2005/0273085 A1 | 12/2005 | Hinman et al. |
| 2006/0041188 A1 | 2/2006 | Dirusso et al. |
| 2006/0094931 A1 | 5/2006 | Danitz et al. |
| 2006/0111209 A1 | 5/2006 | Hinman et al. |
| 2006/0111210 A1 | 5/2006 | Hinman |
| 2006/0111615 A1 | 5/2006 | Danitz |
| 2006/0111616 A1 | 5/2006 | Danitz |

FOREIGN PATENT DOCUMENTS

| | | |
|---|---|---|
| JP | 2005-7068 | 1/2005 |
| JP | 2005/007068 A | 1/2005 |
| WO | WO 97/23158 A1 | 7/1997 |
| WO | WO 2005/079683 A1 | 9/2005 |

OTHER PUBLICATIONS

Notification of Transmittal of the International Search Report and the Written Opinion of the International Searching Authority, or the Declaration dated Sep. 29, 2008 issued in corresponding International Application No. PCT/US2008/063721.

ARTICULATING TORQUEABLE HOLLOW DEVICE

CROSS-REFERENCE TO RELATED CASES

This application is a continuation of U.S. patent application Ser. No. 14/834,717, filed Aug. 25, 2015, which is a continuation of U.S. patent application Ser. No. 13/901,936, filed May 24, 2013, now U.S. Pat. No. 9,144,369, which is a continuation of U.S. patent application Ser. No. 12/121,345, filed May 15, 2008, now U.S. Pat. No. 8,465,420, which claims priority to, and the benefit of, U.S. Provisional Patent Application Ser. No. 60/930,748, filed May 18, 2007, all of which are incorporated herein by reference in their entireties.

TECHNICAL FIELD

The present invention generally relates to medical devices such as endoscopes and catheters. More specifically, the invention relates to flexible medical devices that are bendable and steerable in order to negotiate and access various areas within a patient.

BACKGROUND INFORMATION

It has become well established that there are major public health benefits from early detection and treatment of disease of internal organs (such as the colon, esophagus, stomach, urethra, bladder, ureter, kidney, lungs, bronchi, uterus, and other organ systems) and of various body passageways (such as the alimentary and excretory canals and airways). Early detection of such diseases can be accomplished by periodic medical examinations aided by modern medical procedures and devices such as an endoscope. A conventional imaging endoscope generally comprises a flexible tube with a fiber optic light guide that directs illuminating light from an external light source to the distal tip where it illuminates the region inside the body of the patient to be examined. Frequently, additional optical components are incorporated to adjust the spread of the light exiting the fiber or fiber bundle and the distal tip. An objective lens and fiber optic imaging light guide communicating with a camera at the proximal end of the endoscope, or an imaging camera chip at the distal tip, produce an image that is displayed to the operator. In addition, most endoscopes include one or more working channels through which medical devices such as biopsy forceps, snares, fulguration probes, and other tools may be passed.

Some endoscopes and electrophysiology catheters can steer or deflect the distal tip of the endoscope to follow the pathway of the anatomy under examination such as the colon, bladder, kidney, and heart. Deflection or articulation is often a desirable characteristic in these types of medical devices to minimize friction force and trauma to the surrounding tissue, and to survey targeted examination sites. Navigation of the endoscope through various areas within a patient improves the success of the examination and minimizes pain, side effects, risk, or sedation to the patient.

In order to achieve active deflection at the distal flexible portion of the device, most endoscopes use a force created on one end of the device, usually at a handle. The three is then transmitted to the articulation section by control cables or pull-wires. The pull-wires are carried within the endoscope shaft connecting the distal end to a set of controls in the handle. By manipulating the controls, the operator is able to steer the distal portion of the endoscope during insertion and direct it to a region of interest within the body of the patient.

The mechanism of deflection varies amongst steerable endoscopes and catheters. Some articulating sections are made of elastic elements, such as for example, Pebax®. When the force is applied through the pull-wires, one side of the element can deform (i.e., compress or stretch) resulting in bending. The consistency of bending plane of these devices would depend on such factors as, for example, material homogeneity, or the manufacturing process, for example molding or extrusion. Therefore, the bending consistency with such devices typically is far less than ideal. Also, these devices generally are not designed to transmit a torque from one end to the other. They tend to twist when torqued.

Other articulating designs consist of many separate elements, links, each of which has a pivoting point. Under the applied force, each link would turn around a pivoting point relative to each other. Such devices keep the bending plane much more consistently.

There are many design and performance challenges inherent in these known devices. Some of these challenges include achieving planar deflection at the tip as well as preventing the shaft from buckling or forming a series of "S" shapes from the tension of pull-wire mechanisms. Other challenges include being able to keep an individual bend in one plane, achieving the appropriate amount of angular deflection, and achieving multiple directions of deflection.

Typically, flexible endoscopes are very expensive medical devices. Because of the expense, these endoscopes are built to withstand multiple uses upon many patients and repeated disinfections. Conventional endoscopes are generally built of strong composite material structures such as metals and plastics that do not degrade under repeated cleaning and high temperatures. These material structures decrease the flexibility of the endoscope and can compromise patient comfort. Furthermore, conventional endoscopes are typically complex and fragile instruments that frequently need expensive repair as a result of damage during use or during a disinfection procedure.

SUMMARY OF THE INVENTION

To address or overcome problems with known flexible endoscopes, the invention relates generally to low cost flexible endoscopes that can be used for a single procedure and then disposed, thereby eliminating the need for preparation and cleaning between uses. A low cost endoscope according to the invention could be packaged sterile or disinfected and be capable of being used for a single procedure without endoscope preparation, and then discarded after the single use. The endoscope could include one or more of the following features, as compared to current flexible endoscopes; better navigation and tracking, a superior interface with the operator, improved access by reduced frictional forces upon the lumenal tissue, increased patient comfort, greater clinical productivity and patient throughput than is currently available with a conventional endoscope, a lower risk of cross-contamination, and the ability to be used across more procedures.

It thus is desirable to provide new devices with active controlled bending and methods for using such devices and also for making flexible shafts for medical devices. It is particularly desirable to provide such devices and methods that would achieve planar deflection at the tip as well as preventing the shaft (non-deflecting portion) from buckling or forming a series of "S" shapes from the tension of pull wire mechanisms in comparison to prior art devices. It also is desirable to provide such a device that would be able to keep an individual bend in one plane, achieve the appropriate amount of angular deflection and achieve multiple directions of deflection. Such deflection devices are simpler in construction and less costly than prior art devices, and such methods do not require highly skilled users to utilize the device.

A particular embodiment of the present invention relates to an articulating mechanism for use in a medical device, and the mechanism includes a series of stacked links disposed adjacent to one another and movable with respect to each other. Each link has a front face tapered to a pair of pivot points and a rear face defining a wedge shaped recess for receiving the pivot points of the adjacent link. One or more pull-wires provide tension, holding the stacked links together while also allowing controlled bending of the distal portion by movement of the one or more of the pull-wires.

In an alternative embodiment of the present invention, an articulation mechanism for use in a medical device includes a series of stacked links disposed adjacent to one another and movable with respect to each other. Each link has a front face tapered to a pair of pivot points and a rear face defining a wedge shaped recess for receiving the pivot points of the adjacent link radially offset from the pivot points, allowing for multiple planes of deflection. At least one pull-wire provides tension and holds the stacked links together while also allowing controlled bending of the distal portion by movement of the pull-wire(s).

In another alternative embodiment of the present invention, an articulation mechanism for use in a medical device includes a first articulation section with a first series of stacked links disposed adjacent to one another and movable with respect to each other. Each link has a front face tapered to a pair of pivot points and a rear face defining a wedge shaped recess for receiving the pivot points of the adjacent link. The articulation mechanism also includes a second articulation section. The second articulation section includes a second series of stacked links disposed adjacent to one another and movable with respect to each other, each link having a front face tapered to a pair of pivot points and a rear face defining a wedge shaped recess for receiving the pivot points of the adjacent link. The wedge shaped recesses of the first articulation section are radially offset from the wedge shaped recesses of the second articulation section allowing for multiple planes of deflection.

The articulating mechanism can further include a control cam. The proximal ends of the at least one pull-wire is connected to the control cam. When the user rotates the control cam, tension is applied to the at least one pull-wire thereby deflecting the distal end of the articulation mechanism.

The articulation mechanism can further include an outer sleeve disposed on the outside of the articulation mechanism to provide a smooth exterior surface. A variety of lubrications and/or drug coatings can also be included on the outer sleeve to reduce friction or treat portions of the patient being examined.

The articulating mechanism can further include radiopaque markers or radiopaque materials to ensure proper positioning of the articulating mechanism.

BRIEF DESCRIPTION OF THE DRAWINGS

For a fuller understanding of the nature and operation of various embodiments according to the present invention, reference is made to the following description taken in conjunction with the accompanying drawing figures wherein like reference characters denote corresponding parts throughout the several views and wherein.

DESCRIPTION

The present invention relates to a flexible articulation mechanism to be used in steerable endoscopes and catheters. These medical devices allow an operator to access and view internal body anatomy of a patient as well as to insert surgical instruments into the patient's body. In addition, these devices may include integrated diagnostic and therapeutic capabilities to allow the operator to treat the patient in a single procedure. An articulation mechanism according to the present invention can be sufficiently inexpensive to manufacture such that the device can be considered a single use, disposable item. All relative descriptions herein such as top, bottom, left, right, up, and down are with reference to the figures, and thus should not be construed in a limiting sense.

Figure 1:
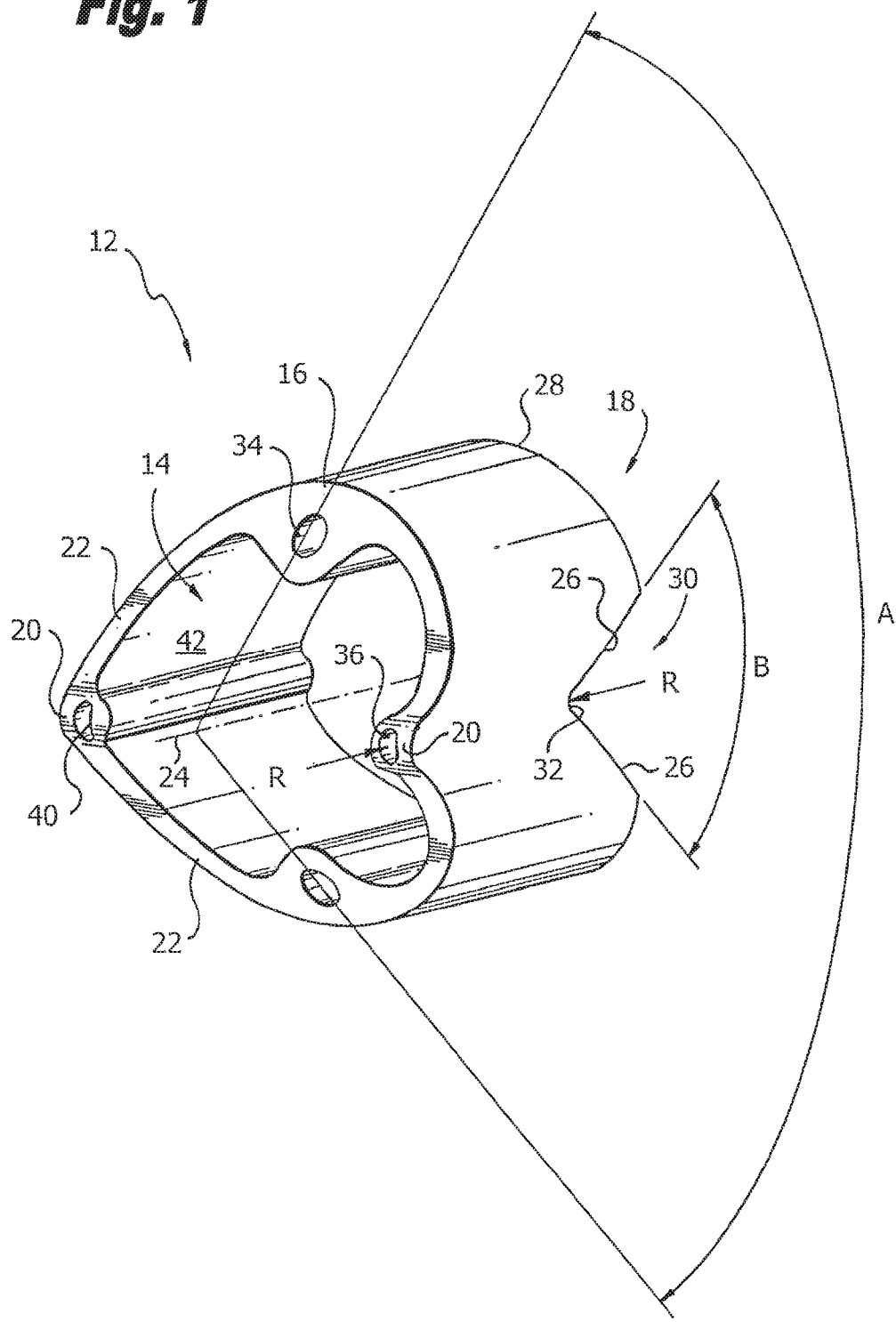
FIG. 1 depicts a link used to form an articulation mechanism in accordance with an embodiment of the present invention.
Figure 2:
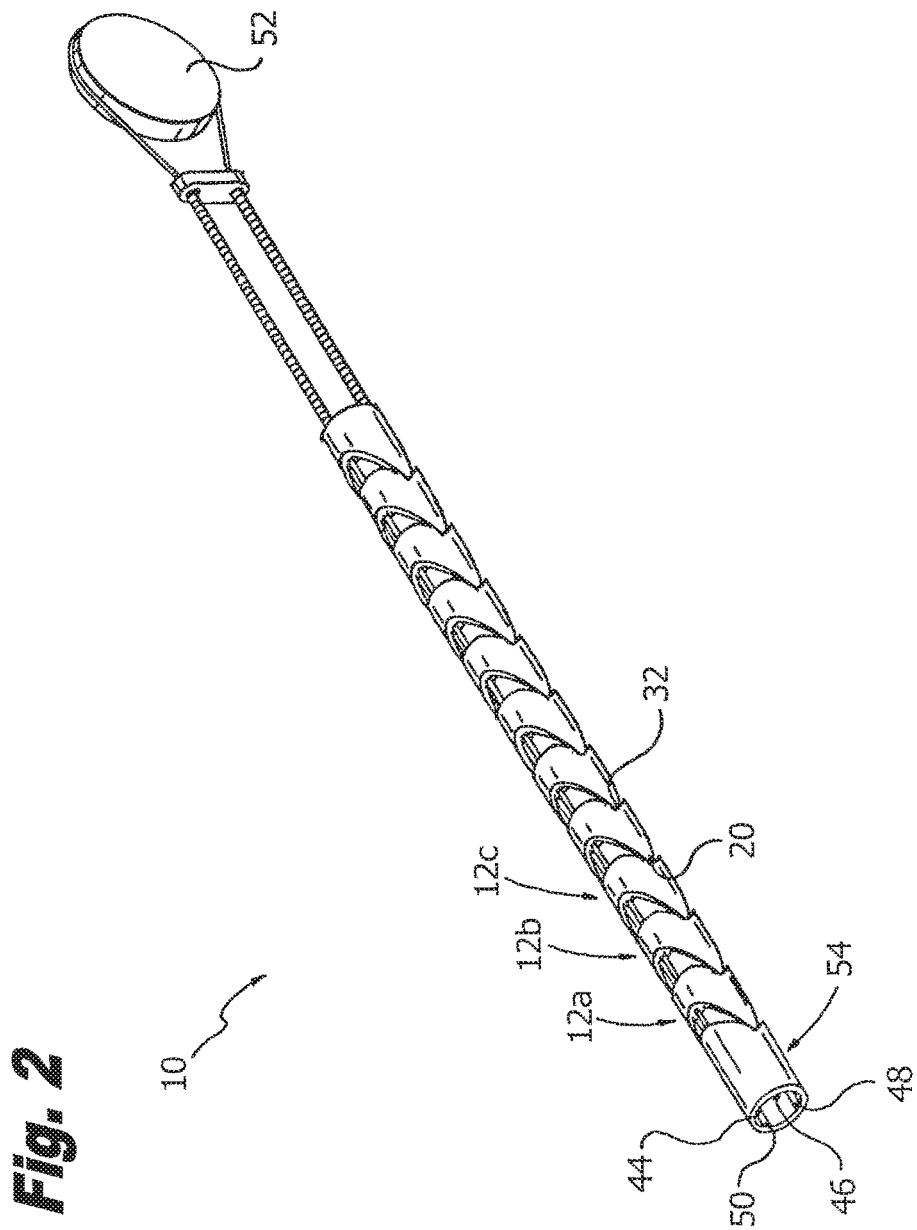
FIG. 2 depicts a schematic rendering of an articulation mechanism formed by stacking a series of the links shown in FIG. 1.

One embodiment of articulation mechanism 10 according to the present invention is made of a series of stacked links 12 that are positioned adjacent to one another, defining an inner lumen 14 and movable with respect to each other. Referring now to FIG. 1, a link 12 according to one embodiment of the present invention includes a front face 16 and a rear face 18. Each link may be deep drawn, rolled and welded, stamped, injection molded, or otherwise formed of stainless-steel or other biocompatible material that allows the link 12 to be rigid while having a thin wall profile in order to maximize the size of the inner lumen 14.

The front face 16 of the link 12 includes a pair of oppositely arranged engagement surfaces that bisect the link 12 and define a pair of pivot points 20 that engage the corresponding rear face 18 of an adjacent link 12. The pivot points 20 are rounded over forming substantially cylindrical surfaces that serve as bearings. The front face 16 of the link 12 further includes two tapered sections 22 that are angled proximally away from the pivot point 20. The two tapered sections 22 are oriented at an angle of A° with respect to the longitudinal axis 24 of the link 12. The terms proximal and distal require a point of reference. In this application, the point of reference is the perspective of the user. Therefore, the term proximal will always refer to an area closest to the user, whereas distal will always refer to an area away from the user.

Similarly, the rear face 18 of the link 12 includes two sloped sections 26 that are angled distally away from a relatively flat surface 28 of the rear face 18 forming a wedge shaped recess 30 with a vertex 32 for receiving the pivot points 20 of the adjacent link 12. As with the tapered sections 22 at the front face 16 of the link, the sloped sections 26 of the rear face 18 are oriented at an angle of B° with respect to the longitudinal axis 24. Additionally, the vertex 32 is rounded to form a substantially cylindrical surface to engage the rounded over surface of the pivot points 20.

A plurality of wire channels 34, 36, 38, 40 are integrally formed in the link 12 itself or otherwise disposed on the inner surface 42 of the link 12. The wire channels are radially spaced at predetermined distances around the circumference of the link 12. As shown in FIG. 1, channels 36 and 40 are positioned at the pivot points 20, while channels 34 and 38 (not shown) are rotated 90° with respect to channels 36 and 40.

Referring now to FIGS. 2-5, the articulation mechanism 10 is created by stacking a number of links 12a, 12b, 12c, etc., such that that the pivot points 20 of each link 12 are aligned with the vertex 32 of the adjacent link 12. Locking pull-wires 46 and 50 disposed in wire channels 36 and 40 provide tension to hold adjacent links 12a, 12b, 12c, etc., together while pull-wires 44 and 48 are components of the control mechanism for bending the articulation mechanism 10 in the desired direction.

Figure 3:
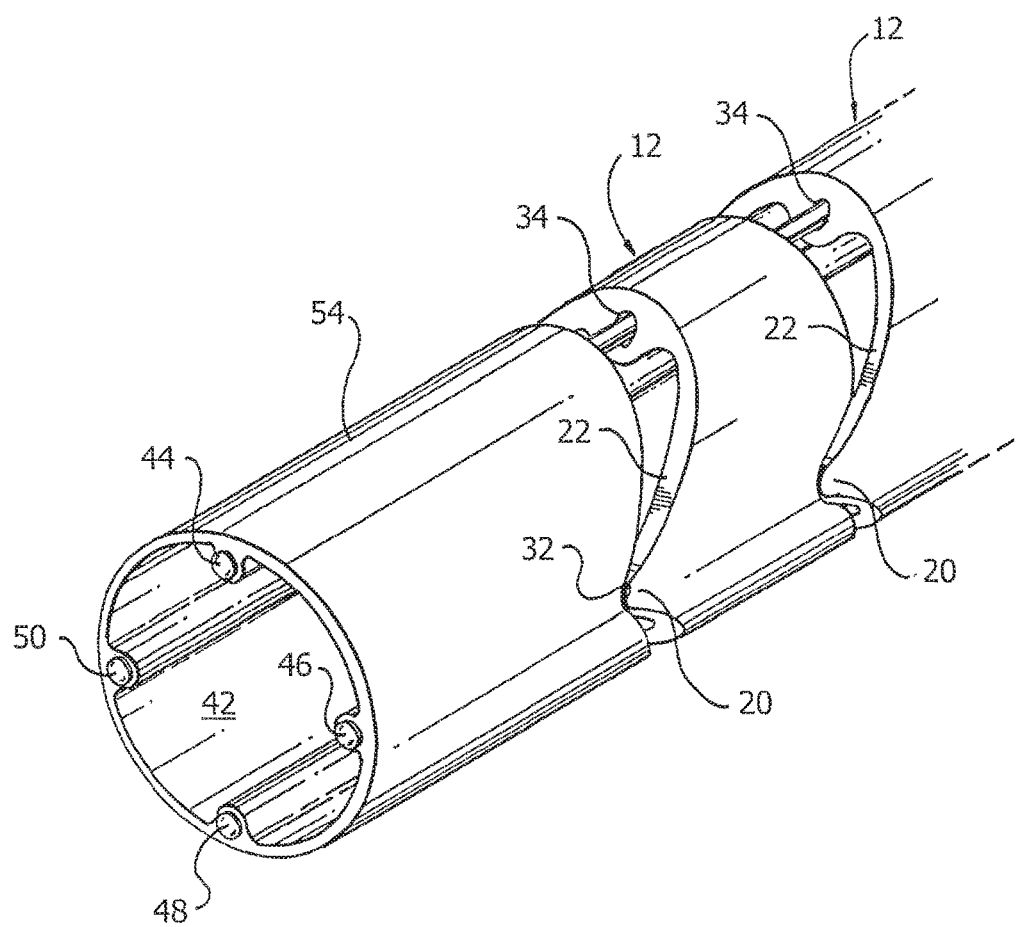
FIG. 3 depicts an enlarged schematic rendering of the distal portion of the articulation mechanism shown in FIG. 2.
Figure 4:
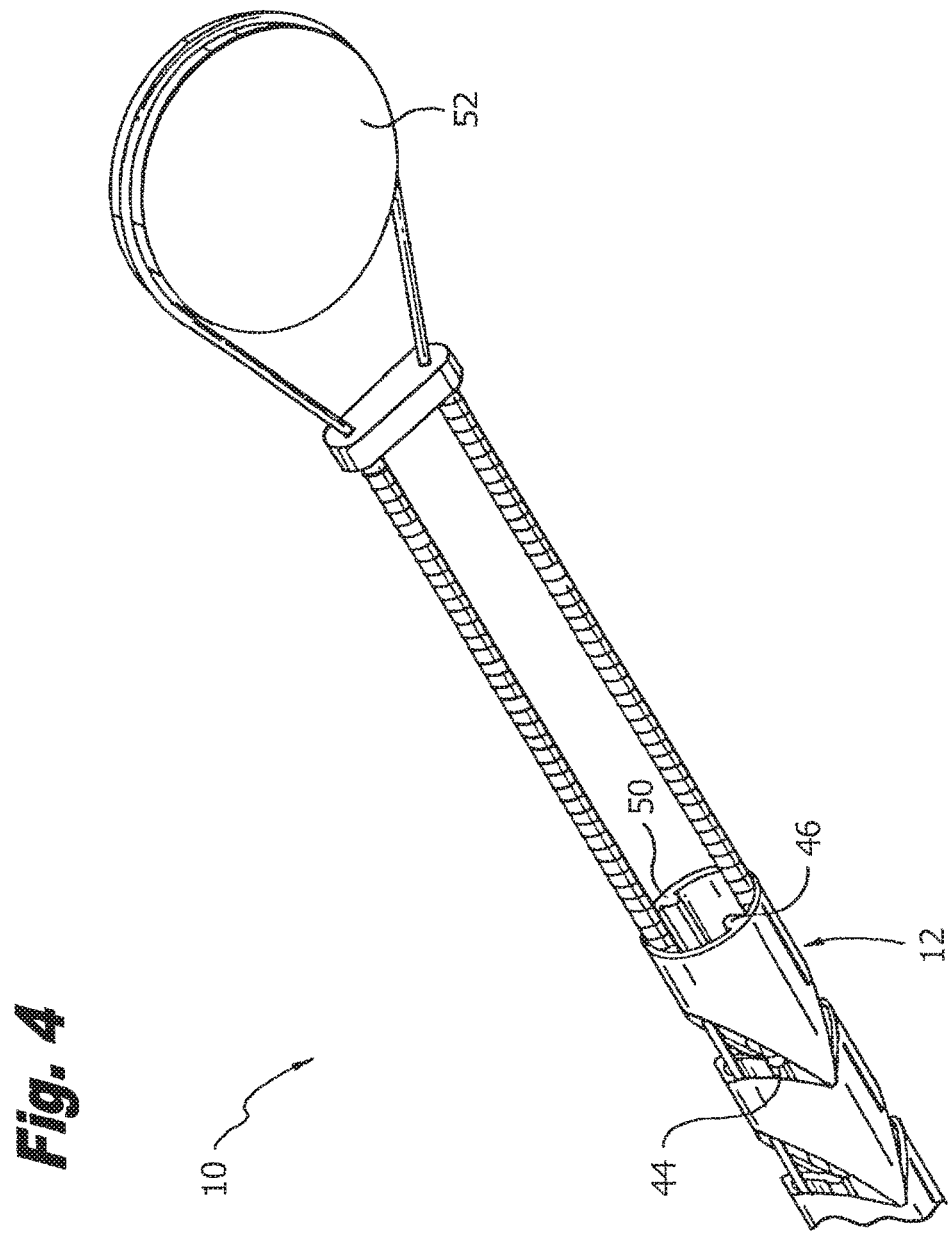
FIG. 4 depicts an enlarged schematic rendering of the proximal portion of the articulation mechanism shown in FIG. 2.
Figure 5:
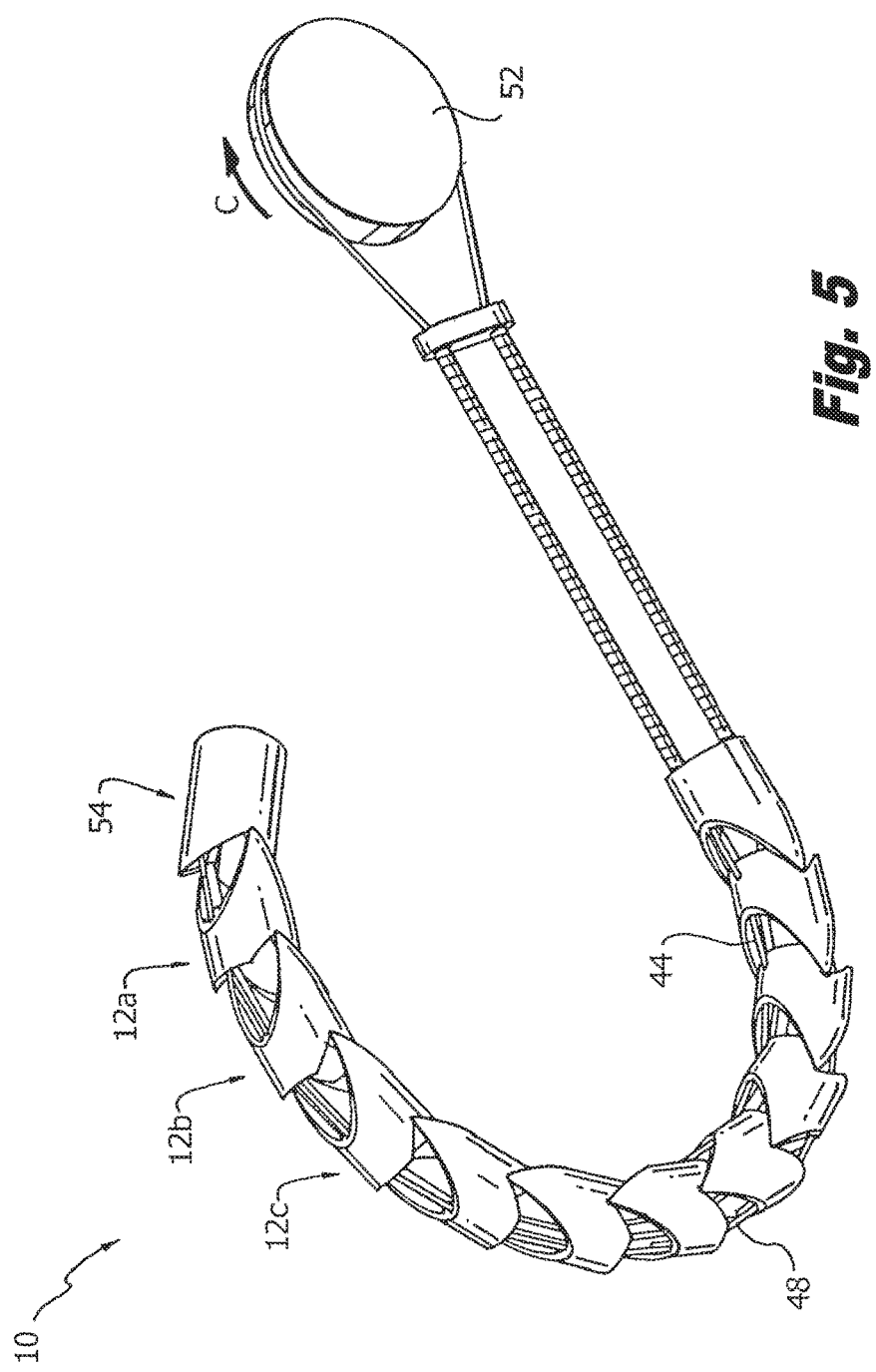
FIG. 5 depicts a schematic rendering of the articulation mechanism shown in FIG. 2 bent in the upward direction.

The control mechanism includes pull-wires 44 and 48 and a control earn 52. The proximal ends of pull-wires 44 and 48 are connected to the control cam 52 and the distal ends of the pull-wires 44 and 48 are connected to the distal end 54 of the articulation mechanism 10 (FIG. 3). As shown in FIG. 5, when the user rotates the control cam 52 in the clockwise direction as indicated by line C on, tension is applied to pull-wire 44, and tension is released from pull-wire 48, thereby deflecting the distal end 54 of the articulation mechanism in an upward direction. Conversely, when the user rotates the control cam 52 in a counter-clockwise direction, tension is applied to pull-wire 48 and released from pull-wire 44, thereby deflecting the distal end 54 in a downward direction.

The deflection capability of the articulation mechanism 10 is a function of the difference between angels A and B and the number of links N, which can be represented by the formula: deflection angle=(A−B)/2×(N−1). For example, in the embodiment shown in FIG. 2, if angle A is 140°, angle B is 100°, and there are 11 links including the first and last link the deflection would be 200°. The radius of deflection is a function of the angle difference and the length of the link (i.e, shorter links will produce a smaller bend radius).

A flexible outer sleeve may be disposed on the outside of the articulation mechanism 10 to provide a smooth exterior surface. The outer sleeve can be made from soft, thin polyurethane, LLDPE, silicon, pellethane, polyurethane, or other approved biocompatible materials such as polyethylene, polypropylene or polyvinyl alcohol. Additionally, the outer sleeve can be coated with a hydrophilic, lubricious coating such as HYDROPASS™ hydrophilic coating available from Boston Scientific Corporation, of Natick, Mass., and described in U.S. Pat. Nos. 5,702,754 and 6,048,620, which are herein incorporated by reference. Additionally, the outer sleeve can be coated with a drug agent to treat internal body tissues.

To ensure proper positioning, it is desirable for the articulation mechanism 10 to be visible using fluoroscopy, echocardiography, intravascular ultrasound, angioscopy, or another means of visualization. Where fluoroscopy is utilized, any or all of the articulation mechanism may be coated with a radiopaque material, or a radiopaque marker may be included on any portion of the device that would be useful to visualize. One example of a radiopaque material that can be used is barium sulfate. Radiopaque markers can be made from any of a number of materials including, for example, gold, platinum, or tungsten.

Figure 6:
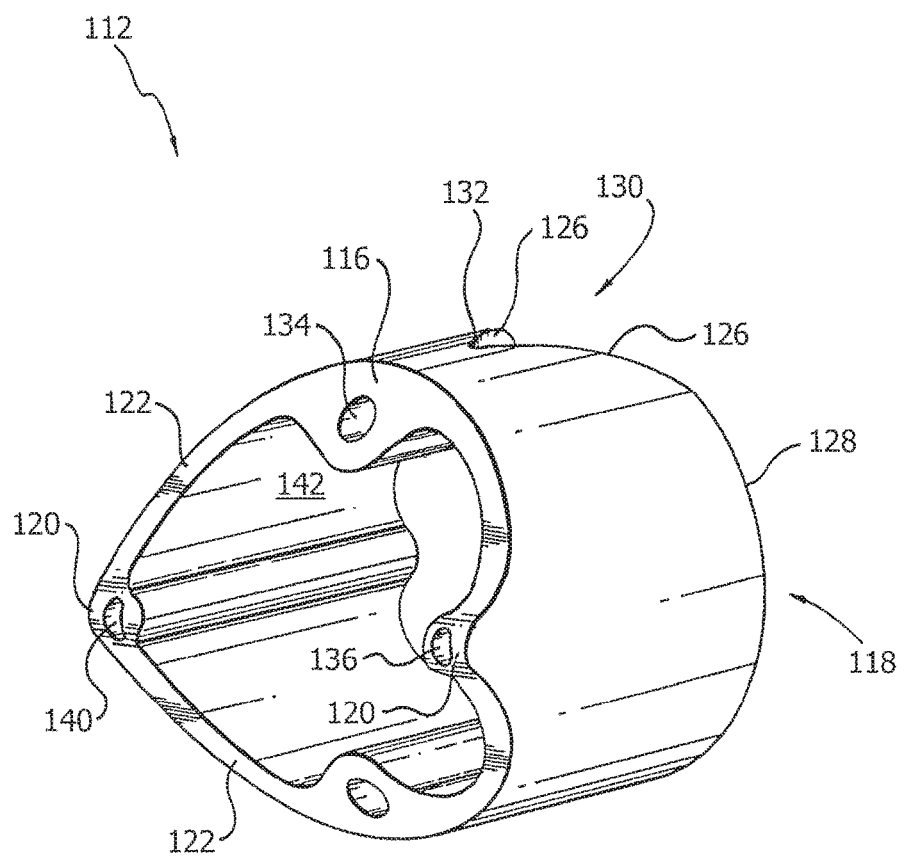
FIG. 6 depicts a link used to form an articulation mechanism in accordance with an alternative embodiment of the present invention.

Referring now to FIG. 6, a link 112 according to an alternative embodiment of the present invention is shown. The link 112 performs substantially the same function as the link 12 described above, and therefore like reference numerals preceded by the numeral "1" are used to indicate like elements.

In this embodiment the front face 116 of the link 112 includes a pair of oppositely arranged engagement surfaces that bisect the link 112 and define a pair of pivot points 120 that engage the corresponding rear face 118 of an adjacent link 112. The pivot points 120 are rounded over forming substantially cylindrical surfaces that serve as bearings. The front face 116 of the link 112 further includes two tapered sections 122 that are angled proximally away from the pivot point 120.

The rear face 118 of the link 112 includes two sloped sections 126 that are angled distally away from a relatively flat surface 128 of the rear face 118 forming a wedge shaped recess 130 with a vertex 132 for receiving the pivot points 120 of the adjacent link 112. Unlike the embodiment discuss above, the wedge shaped recess 130 is radially offset 90° with respect to the tapered sections 122 of the front face 116. The vertex 132 is rounded to form a substantially cylindrical surface to engage the rounded over surface of the pivot points 120.

A plurality of wire channels 134, 136, 138, 140 are integrally formed in the link 112 itself or otherwise disposed on the inner surface 142 of the link 112. The wire channels are radially spaced at predetermined distances around the circumference of the link 112. As shown in FIG. 6, channels 136 and 140 are positioned at the pivot points 120, while channels 134 and 138 (not shown) are rotated 90° with respect to channels 136 and 140 and are positioned at the vertex 132 of the wedge shaped recess 130.

Figure 7:
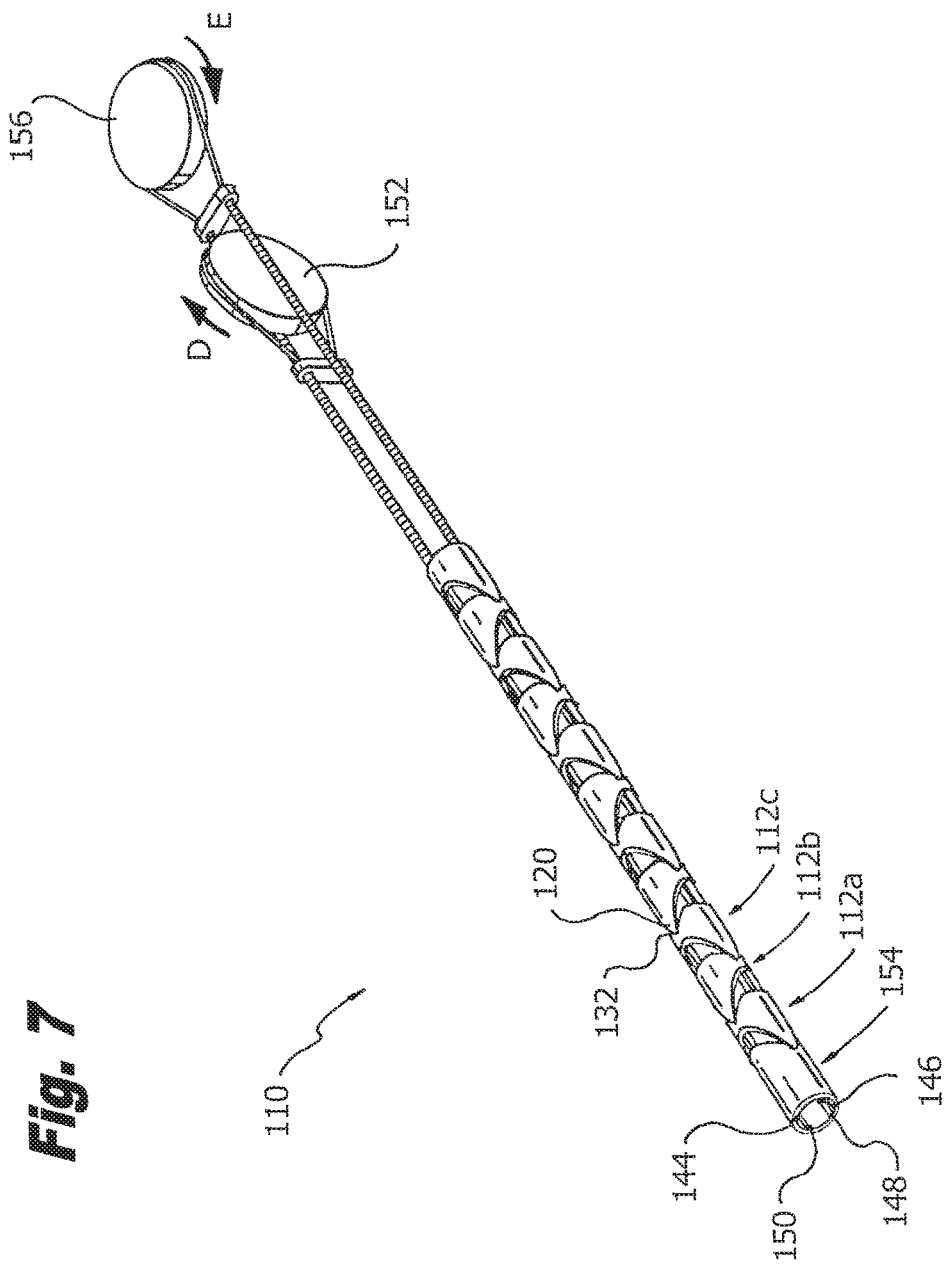
FIG. 7 depicts a schematic rendering of an articulation mechanism formed by stacking a series of the links shown in FIG. 6.

Referring now to FIG. 7, the articulation mechanism 110 is created by stacking a number of links 112a, 112b, 112c, etc., such that that the pivot points 120 of each link 112 are aligned with the vertex 132 of the adjacent link 112. Since the front tapered section 122 and the wedge shaped recess 130 are perpendicular to each other, each sequential element turns the bending plane 90° so bending happens in pairs of elements.

The control mechanism includes pull-wires 144, 146, 148, 150 and two control cams 152 and 156. The proximal ends of pull-wires 144 and 148 are connected to control cam 152 and the distal ends of the pull-wires 144 and 148 are connected to the distal end 154 of the articulation mechanism 110. The proximal ends of pull-wires 146 and 150 are connected to control cam 156 and the distal ends of the pull-wires 146 and 150 are connected to the distal end 154 of the articulation mechanism 110. When the user rotates the control cam 152 in the clockwise direction as indicated by line D, tension is applied to pull-wire 144, and tension is released from pull-wire 148, thereby deflecting the distal end 154 of the articulation mechanism 110 in an upward direction. Conversely, when the user rotates the control cam 152 in a counter-clockwise direction, tension is applied to pull-wire 148 and released from pull-wire 144, thereby deflecting the distal end 154 in a downward direction. When the user rotates the control cam 156 in the clockwise direction as indicated by line E, tension is applied to pull-wire 150, and tension is released from pull-wire 146, thereby deflecting the distal end 154 of the articulation mechanism to the right. Conversely, when the user rotates the control cam 156 in a counter-clockwise direction, tension is applied to pull-wire 146 and released from pull-wire 150, thereby deflecting the distal end 154 to the left.

Figure 8:
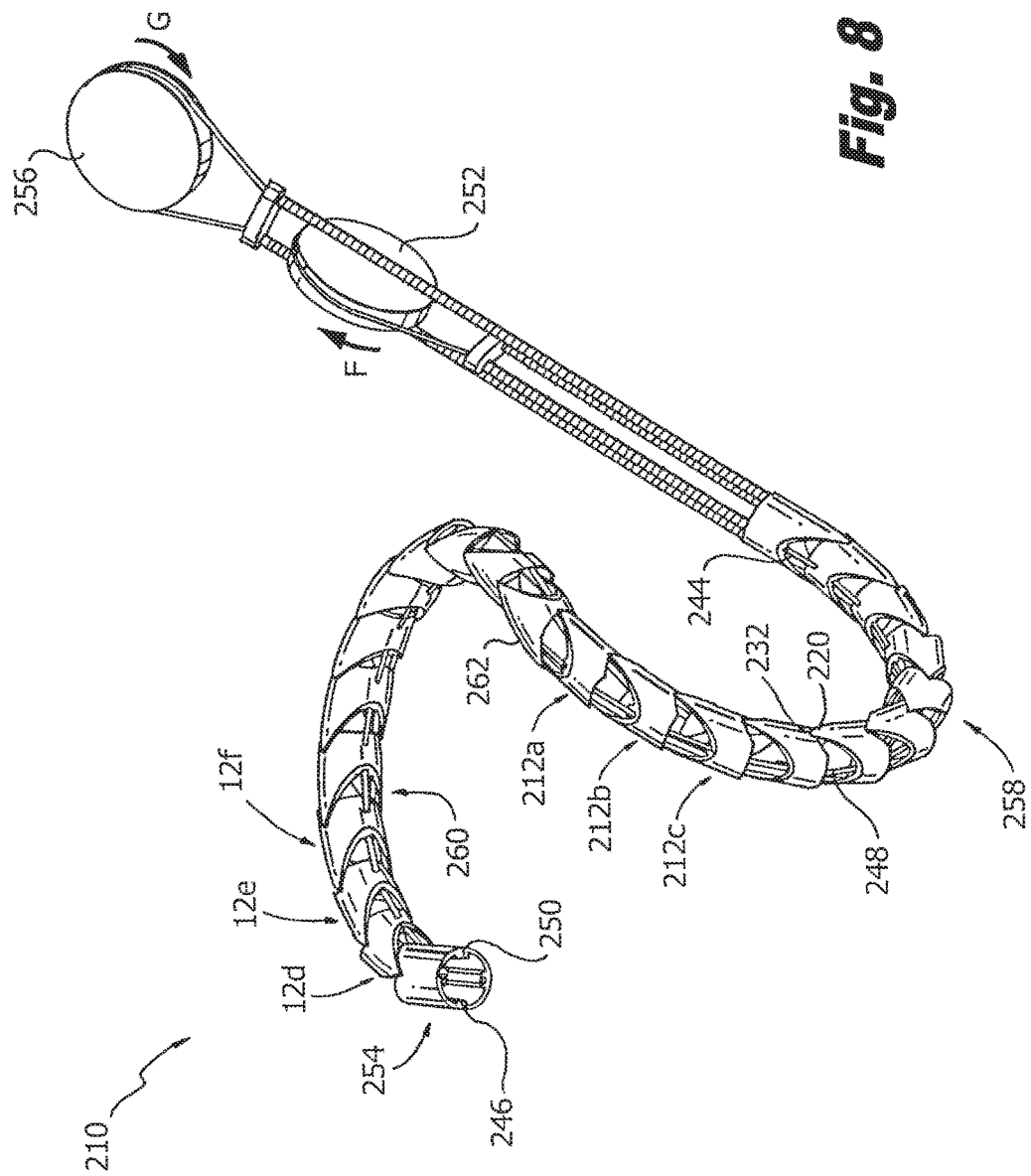
FIG. 8 depicts a link used to form an articulation mechanism in accordance with an alternative embodiment of the present invention.

Referring now to FIG. 8, an articulation mechanism 210 according to an alternative embodiment of the present invention is shown. The articulation mechanism 210 performs substantially the same function as the articulation mechanism 10 described above, and therefore like reference numerals preceded by the numeral "2" are used to indicate like elements.

In this embodiment, a combination of links are used to make the articulation mechanism 210. The first articulation section 258 closest to the control mechanism is created by stacking a number of links 212a, 212b, 212c, etc. such that the pivot points 220 of each link 212 are aligned with the vertex 232 of the adjacent link 212. On the distal side of link 212a, a transition link 262 is inserted thereby rotating the bending angle 90°. The second articulation section 260 on the distal side of link 262 is then created by stacking a number of links 212d, 212e, 212f, etc. creating two planes of deflection.

The control mechanism includes pull-wires 244, 246, 248, 250 and two control cams 252 and 256. The proximal ends of pull-wires 244 and 248 are connected to control cam 252 and the distal ends of the pull-wires 244 and 248 are connected to the transition link 262. The proximal ends of pull-wires 246 and 250 are connected to control cam 256 and the distal ends of the pull-wires 246 and 250 are connected to the distal end 254 of the articulation mechanism 210. When the user rotates the control cam 252 in the clockwise direction as indicated by line F, tension is applied to pull-wire 244, and tension is released from pull-wire 248, thereby deflecting the first deflection section 258 of the articulation mechanism in an upward direction. Conversely, when the user rotates the control cam 252 in a counter-clockwise direction, tension is applied to pull-wire 248 and released from pull-wire 244, thereby deflecting the first deflection section 258 in a downward direction. When the user rotates the control cam 256 in the clockwise direction as indicated by line G, tension is applied to pull-wire 250, and tension is released from pull-wire 246, thereby deflecting the second deflection section 260 of the articulation mechanism to the right. Conversely, when the user rotates the control cam 256 in a counter-clockwise direction, tension is applied to pull-wire 246 and released from pull-wire 250, thereby deflecting the second deflection section 260 to the left.

Figure 9:
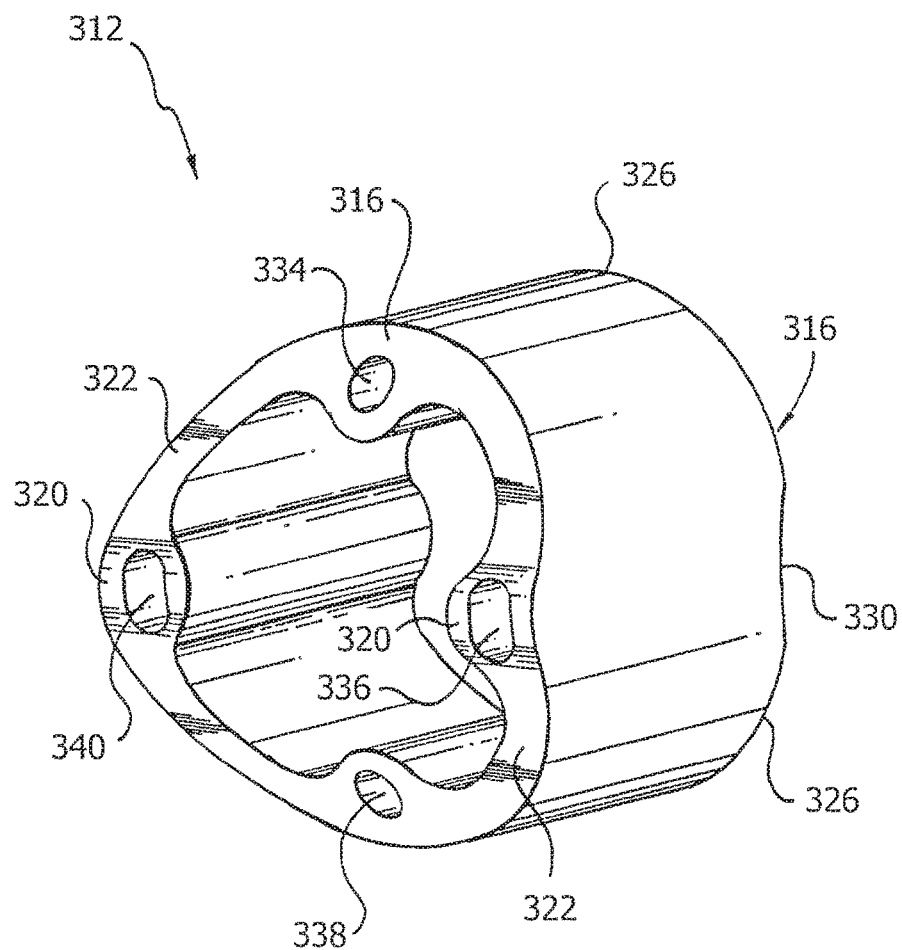
FIG. 9 depicts a link used to form an articulation mechanism in accordance with an alternative embodiment of the present invention.

Referring now to FIG. 9, a link 312 according to an alternative embodiment of the present invention is shown. The link 312 performs substantially the same function as the link 12 described above, and therefore like reference numerals preceded by the numeral "3" are used to indicate like elements.

In this embodiment the front face 316 of the link 312 includes a pair of oppositely arranged engagement surfaces that bisect the link 312 and define a pair of pivot points 320 that engage the corresponding rear face 318 of an adjacent link. The pivot points 320 are rounded over forming substantially cylindrical surfaces that serves as bearings. The front face 316 of the link 312 further includes two tapered sections 322 that are angled proximally away from the pivot point 320.

The rear face 318 of the link 312 includes two sloped sections 326 that are angled distally away from a relatively flat surface 328 of the rear face 318 forming a wedge shaped recess 330 with a vertex 332 for receiving the pivot points 320 of an adjacent link. The vertex 332 is rounded to form a substantially cylindrical surface to engage the rounded over surface of the pivot points 320.

A plurality of wire channels 334, 336, 338, 340 are integrally formed in the link 312 itself or otherwise disposed on the inner surface 342 of the link 312. The wire channels are radially spaced at predetermined distances around the circumference of the link 312. As shown in FIG. 9, channels 336 and 340 are positioned at the pivot points 320, while channels 334 and 338 are rotated 90° with respect to channels 336 and 340 and are positioned at the vertex 332 of the wedge shaped recess 330.

Figure 10:
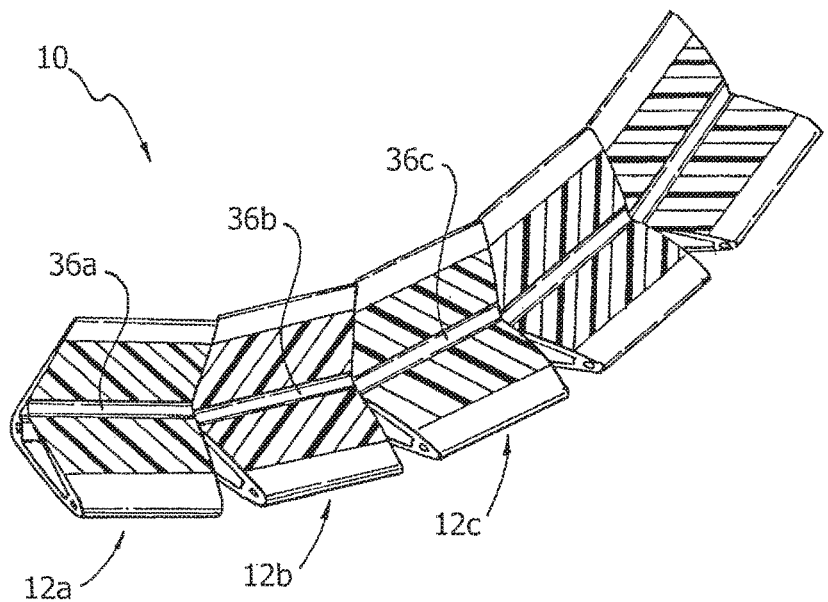
FIG. 10 depicts a partial cross-section of an articulation mechanism formed by stacking a series of the links shown in FIG. 1 in a deflected position.

Unlike the embodiment of the link 12 described above, the wire channels 336 and 340 are chamfered or otherwise elongated to allow for greater lateral movement of the pull-wires when the articulation mechanism is deflected. For example, referring now to FIG. 10, the articulation mechanism 10 created by stacking a number of links 12a, 12b, 12c, etc. is shown in a deflected position. In this deflected position, the wire channels 36a, 36b, 36c, etc. are partially misaligned and pull-wires can jam or be pinched between adjacent links 12.

Figure 11:
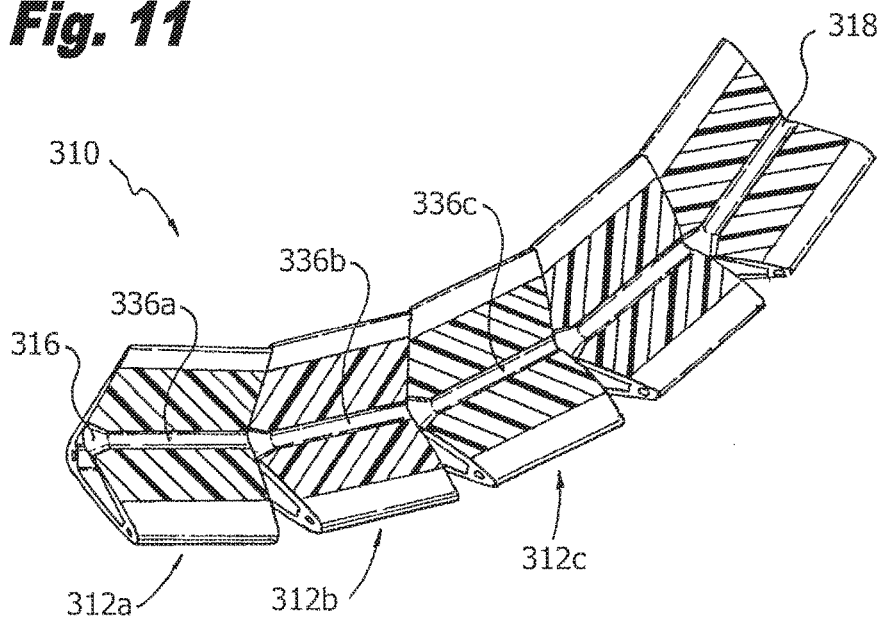
FIG. 11 depicts a partial cross-section of an articulation mechanism formed by stacking a series of the links shown in FIG. 9 in a deflected position.

Referring now also to FIG. 11, the articulation mechanism 310 created by stacking a number of links 312a, 312b, 312c, etc. is shown in a deflected position. In this embodiment, the wire channels 336a, 336b, 336c, etc. remain in alignment after deflection due to the chamfering of the wire channels 336. The wire channels 336 can be chamfered at the front face 316, the rear face 318, or both. Alternatively, the wire channels 336 can be elongated along their entire length instead of chamfering at one or both ends.

Additional deflection sections and/or pull-wires could be included in the control mechanism depending on how many planes of deflection are desired. The pull-wires 44, 46, 48, 50 are made from stainless steel, polymer filaments, strong textile or synthetic material such as kevlar or nylon, or other metals and alloys such as, for example, Nitinol®, which is a nickel-titanium alloy. The control mechanism may also include handles, levers, knobs, robotics, a joystick, or other control features, none of which are shown but all of which would be known to those knowledgeable about medical devices.

The disclosed embodiments are exemplary. The invention is not limited by or only to the disclosed exemplary embodiments. Also, various changes to and combinations of the disclosed exemplary embodiments are possible and within this disclosure.

What is claimed is:
1. An articulation mechanism for use in a medical device, comprising;

a first series of stacked links disposed adjacent to one another and movable with respect to each other, each link of the first series of stacked links extending along a longitudinal link axis and including:
   a front face defining a pair of pivot points; and
   a rear face defining a wedge shaped recess for receiving the pivot points of the adjacent link, the wedge shaped recess and pivot points of the first series of stacked links being aligned circumferentially;
a second series of stacked links disposed adjacent to one another and movable with respect to each other, each link of the second series of stacked links extending along a longitudinal link axis and including:
   a front face defining a pair of pivot points; and
   a rear face defining a wedge shaped recess for receiving the pivot points of the adjacent link, the wedge shaped recess and pivot points of the second series of stacked links being aligned circumferentially; and
a base link extending proximally of the first series of stacked links, the base link including a proximal end face extending entirely along a plane perpendicular to a longitudinal base link axis and a pair of distally extending projections configured to be received within the wedge shaped recess of a proximal-most link of the first series of stacked links;
wherein the wedge shaped recesses of the first series of stacked links are radially offset from the wedge shaped recesses of the second series of stacked links.

2. The articulation mechanism of claim 1, further including at least one pull-wire extending through the first series of stacked links and the second series of stacked links.

3. The articulation mechanism of claim 2, further including a control cam connected to the at least one pull-wire.

4. The articulation mechanism of claim 2, wherein each link of the first series of stacked links and the second series of stacked links includes a lumen extending through a respective pivot point thereof, wherein the at least one pull-wire extends through the lumen.

5. The articulation mechanism of claim 1, further comprising an outer sleeve disposed on an outer surface of the articulation mechanism.

6. The articulation mechanism of claim 1, wherein each link of the first series of stacked links and the second series of stacked links includes a rear face surface extending perpendicular to a respective longitudinal link axis.

7. The articulation mechanism of claim 1, further including a terminating link extending distally of the second series of stacked links, the terminating link including a surface extending entirely along a plane perpendicular to the a longitudinal terminating link axis and a rear face defining a wedge shaped recess, the wedge shaped recess of the terminating link configured to receive therein the pair of pivot points of a distal-most link of the second series of stacked links.

8. An articulation mechanism for use in a medical device, comprising;
a first series of stacked links disposed adjacent to one another and movable with respect to each other, each link of the first series of stacked links extending along a longitudinal link axis and including:
   a front face defining a pair of pivot points; and
   a rear face defining a wedge shaped recess for receiving the pivot points of the adjacent link, the wedge shaped recess and pivot points of the first series of stacked links being aligned circumferentially; and
   a pair of lumens extending through each pivot point;
a second series of stacked links disposed adjacent to one another and movable with respect to each other, each link of the second series of stacked links extending along a longitudinal link axis and including:
   a front face defining a pair of pivot points; and
   a rear face defining a wedge shaped recess for receiving the pivot points of the adjacent link, the wedge shaped recess and pivot points of the second series of stacked links being aligned circumferentially; and
   a pair of lumens extending through each pivot point; and
a terminating link extending distally of the second series of stacked links, the terminating link including a surface extending entirely along a plane perpendicular to a longitudinal terminating link axis and a rear face defining a wedge shaped recess, the wedge shaped recess of the terminating link configured to receive therein the pair of pivot points of a distal-most link of the second series of stacked links;
wherein the wedge shaped recesses of the first series of stacked links are radially offset from the wedge shaped recesses of the second series of stacked links.

9. The articulation mechanism of claim 8, further including a pair of pull-wires, each pull-wire extending through the a lumen of the pair of lumens of the first series of stacked links and the second series of stacked links.

10. The articulation mechanism of claim 9, further including a control cam connected to the pair of pull-wires.

11. The articulation mechanism of claim 8, wherein in an articulated configuration, the second series of stacked links extends in a first plane and the second series of stacked links extends in a second plane angled with respect to the first plane.

12. The articulation mechanism of claim 8, further including a base link extending proximally of the first series of stacked links, the base link including a proximal end face extending entirely along a plane perpendicular to a longitudinal base link axis and a pair of distally extending projections configured to be received within the wedge shaped recess of a proximal-most link of the first series of stacked links.

13. An articulation mechanism for use in a medical device, comprising;
a first series of stacked links disposed adjacent to one another and movable with respect to each other, each link of the first series of stacked links extending along a longitudinal link axis and including:
   a front face defining a pair of pivot points; and
   a rear face defining a wedge shaped recess for receiving the pivot points of the adjacent link, the wedge shaped recess and pivot points of the first series of stacked links being aligned circumferentially;
a second series of stacked links disposed adjacent to one another and movable with respect to each other, each link of the second series of stacked links extending along a longitudinal link axis and including:
   a front face defining a pair of pivot points; and
   a rear face defining a wedge shaped recess for receiving the pivot points of the adjacent link, the wedge shaped recess and pivot points of the second series of stacked links being aligned circumferentially; and
a terminating link extending distally of the second series of stacked links, the terminating link including a surface extending entirely along a plane perpendicular to a longitudinal terminating link axis and a rear face defining a wedge shaped recess, the wedge shaped recess of the terminating link configured to receive therein the pair of pivot points of a distal-most link of the second series of stacked links;

wherein the wedge shaped recesses of the first series of stacked links are radially offset from the wedge shaped recesses of the second series of stacked links; and wherein in an articulated configuration, the second series of stacked links extends in a first plane and the second series of stacked links extends in a second plane angled with respect to the first plane.

14. The articulation mechanism of claim 13, further including a base link extending proximally of the first series of stacked links, the base link including a proximal end face extending entirely along a plane perpendicular to a longitudinal base link axis and a pair of distally extending projections configured to be received within the wedge shaped recess of a proximal-most link of the first series of stacked links.

15. The articulation mechanism of claim 13, further including at least one pull-wire extending through the first series of stacked links and the second series of stacked links.

16. The articulation mechanism of claim 15, further including a control cam connected to the at least one pull-wire.

17. The articulation mechanism of claim 13, wherein each link of the first series of stacked links and the second series of stacked links includes a rear face surface extending perpendicular to a respective longitudinal link axis.

* * * * *